US010774000B2

(12) United States Patent
Ong et al.

(10) Patent No.: US 10,774,000 B2
(45) Date of Patent: *Sep. 15, 2020

(54) ADMIXTURE AND METHOD FOR FREEZE-THAW DAMAGE RESISTANCE AND SCALING DAMAGE RESISTANCE OF CEMENTITIOUS COMPOSITIONS

(71) Applicant: Construction Research & Technology GmbH, Trostberg (DE)

(72) Inventors: Frank Shaode Ong, Solon, OH (US); James C. Smith, Cuyahoga Falls, OH (US); Raymond Fete, Aurora, OH (US); Rick Paponetti, Bedford, OH (US)

(73) Assignee: Construction Research & Technology GmbH, Trostberg (DE)

( * ) Notice: Subject to any disclaimer, the term of this patent is extended or adjusted under 35 U.S.C. 154(b) by 65 days.

This patent is subject to a terminal disclaimer.

(21) Appl. No.: 15/019,294

(22) Filed: Feb. 9, 2016

(65) Prior Publication Data

US 2016/0152520 A1 Jun. 2, 2016

Related U.S. Application Data

(63) Continuation of application No. 13/835,467, filed on Mar. 15, 2013, now Pat. No. 9,365,453.

(60) Provisional application No. 61/695,134, filed on Aug. 30, 2012, provisional application No. 61/635,562, filed on Apr. 19, 2012.

(51) Int. Cl.
| | |
|---|---|
| *C04B 16/08* | (2006.01) |
| *C04B 28/02* | (2006.01) |
| *C04B 38/08* | (2006.01) |
| *C04B 40/00* | (2006.01) |
| *C08L 101/14* | (2006.01) |
| *A61L 15/60* | (2006.01) |
| *C04B 38/10* | (2006.01) |
| *C04B 111/20* | (2006.01) |
| *C04B 111/40* | (2006.01) |

(52) U.S. Cl.
CPC ............ *C04B 16/085* (2013.01); *A61L 15/60* (2013.01); *C04B 28/02* (2013.01); *C04B 38/085* (2013.01); *C04B 38/10* (2013.01); *C04B 40/0039* (2013.01); *C08L 101/14* (2013.01); *C04B 2111/29* (2013.01); *C04B 2111/40* (2013.01)

(58) Field of Classification Search
CPC ....... A61L 15/60; C04B 16/085; C04B 28/02; C04B 38/085; C04B 38/10; C04B 40/0039; C04B 2111/29; C04B 2111/40; C04B 16/08; C04B 38/08; C04B 40/00; C08L 101/14

See application file for complete search history.

(56) References Cited

U.S. PATENT DOCUMENTS

| | | | |
|---|---|---|---|
| 2,361,297 | A | 10/1944 | Kutsche |
| 4,005,033 | A | 1/1977 | Georgeau et al. |
| 4,057,526 | A | 11/1977 | De Rook |
| 4,513,106 | A | 4/1985 | Edgren et al. |
| 4,538,733 | A | 9/1985 | Hoffman |
| 4,778,829 | A | 10/1988 | Ichimura et al. |
| 5,016,689 | A | 5/1991 | McGarvey et al. |
| 5,304,303 | A | 4/1994 | Kozak, III |
| 6,084,011 | A | 7/2000 | Lucero et al. |
| 6,133,347 | A | 10/2000 | Vickers, Jr. et al. |
| 6,451,881 | B1 | 9/2002 | Vickers, Jr. et al. |
| 6,492,461 | B1 | 12/2002 | Vickers, Jr. et al. |
| 7,435,766 | B2 | 10/2008 | Ong |
| 7,543,642 | B2 | 6/2009 | Reddy et al. |
| 2004/0144537 | A1 | 7/2004 | Reddy et al. |
| 2005/0061206 | A1 | 3/2005 | Reddy et al. |
| 2005/0274285 | A1 | 12/2005 | Christensen et al. |
| 2005/0284340 | A1 | 12/2005 | Vickers et al. |
| 2006/0281836 | A1 | 12/2006 | Kerns et al. |
| 2007/0098973 | A1 | 5/2007 | Wagner et al. |
| 2007/0137528 | A1 | 6/2007 | Le Roy-Delage et al. |
| 2007/0154711 | A1 | 7/2007 | Masuda et al. |
| 2009/0093558 | A1 | 4/2009 | Madish et al. |
| 2009/0093588 | A1 | 4/2009 | Akutsu et al. |
| 2011/0281984 | A1 | 11/2011 | Zmarsly et al. |
| 2013/0280364 | A1 | 10/2013 | Ong et al. |
| 2013/0281556 | A1 | 10/2013 | Ong et al. |
| 2014/0107238 | A1 | 4/2014 | Ong et al. |
| 2015/0361002 | A1 | 12/2015 | Ong et al. |

FOREIGN PATENT DOCUMENTS

| | | |
|---|---|---|
| DE | 1 961 390 | 6/1971 |
| DE | 10 2006 009 842 A1 | 9/2007 |
| EP | 0 320 473 A1 | 6/1989 |

(Continued)

OTHER PUBLICATIONS

U.S. Appl. No. 13/866,702—Office Action, dated Nov. 18, 2014.
U.S. Appl. No. 13/866,702—Office Action, dated Jun. 10, 2015.
U.S. Appl. No. 14/515,201—Office Action, dated Aug. 21, 2015.
Canadian Patent Application No. 2,869,842—Office Action, dated Feb. 12, 2016.
U.S. Appl. No. 13/866,702—Office Action, dated Aug. 4, 2014.
U.S. Appl. No. 14/560,250—Office Action, dated Mar. 8, 2016.
PCT/EP2015/078633—International Search Report, dated May 4, 2016.
International Preliminary Report on Patentability, dated Oct. 30, 2014, for PCT International Patent Application No. PCT/EP2013/058155.

(Continued)

*Primary Examiner* — Irina S Zemel
(74) *Attorney, Agent, or Firm* — Curatolo Sidoti Co., LPA; Slavatore A. Sidoti

(57) ABSTRACT

A freeze-thaw damage resistance and scaling damage resistance admixture for a cementitious composition including an aqueous slurry comprising a water insoluble superabsorbent polymer and expandable polymeric microspheres. A method for preparing a freeze-thaw damage resistant and scaling damage resistant cementitious composition including forming a mixture of a hydraulic cement and an admixture including an aqueous slurry of a water insoluble superabsorbent polymer and expanded polymeric microspheres.

17 Claims, 2 Drawing Sheets

(56) References Cited

FOREIGN PATENT DOCUMENTS

| EP | 0 950 699 A1 | 10/1999 |
|---|---|---|
| FR | 2072897 | 9/1971 |
| GB | 2 347 413 A | 9/2000 |
| JP | 01271225 A | 10/1989 |
| JP | 2005-254213 A | 9/2005 |
| JP | 5 588880 B2 | 9/2014 |
| WO | WO 03/051793 A2 | 6/2003 |
| WO | WO 2004/056549 A1 | 7/2004 |
| WO | WO 2006/133855 A2 | 12/2006 |
| WO | WO 2009/040359 A1 | 4/2009 |
| WO | WO 2010/070987 A1 | 6/2010 |
| WO | WO 2013/156589 A1 | 10/2013 |
| WO | WO 2013/159043 | 10/2013 |
| WO | WO 2014/198532 | 12/2014 |

OTHER PUBLICATIONS

Memon, et al., "Effect of Sodium Hydroxide Concentration on Fresh Properties and Compressive Strength of Sel-Compacting Geopolymer Concrete", Journal of Engineering Science & Technology, vol. 8, No. 1, pp. 46-56 (2013).
PCT/EP2015/078633—International Written Opinion, dated May 4, 2016.
PCT/EP2013/058155—International Search Report, dated Sep. 2, 2013.
PCT/EP2013/058155—International Written Opinion, dated Sep. 2, 2013.
PCT/EP2013/037455—International Search Report, dated Sep. 2, 2013.
PCT/EP2013/037455—International Written Opinion, dated Sep. 2, 2013.
PCT/EP2013/058156—International Search Report, dated Sep. 2, 2013.
PCT/EP2013/058156—International Written Opinion, dated Sep. 2, 2013.
Moennig, et al., "Water saturated super-absorbent polymers used in high strength concrete", Otto-Graf-Juornal: Annual Journal on Research and Testing of Materials, Jan. 1, 2005, vol. 16, pp. 193-202, Stuttgard, Germany.
European Search Report of European Patent Application No. 15152251.3, dated Aug. 17, 2015.
Jensen, et al., "Water entrain cement-based materials II. Experimental observations", Cement and Concrete Research, 2002, vol. 32, pp. 973-978, Aalborg, Denmark.
PCT/EP2015/078630—International Search Report, dated Mar. 1, 2016.
PCT/EP2015/078630—International Written Opinion, dated Mar. 1, 2016.
PCT/EP2015/078631—International Search Report, dated Feb. 2, 2016.
PCT/EP2015/078631—International Written Opinion, dated Feb. 2, 2016.
PCT/EP2015/078632—International Search Report, dated Feb. 2, 2016.
PCT/EP2015/078632—International Written Opinion, dated Feb. 2, 2016.
U.S. Appl. No. 13/835,467—Office Action, dated Mar. 4, 2014.
U.S. Appl. No. 13/835,467—Office Action, dated Jun. 10, 2014.
U.S. Appl. No. 13/835,467—Office Action, dated Feb. 3, 2015.
U.S. Appl. No. 13/836,495—Office Action, dated Feb. 20, 2015.
U.S. Appl. No. 13/835,467—Office Action, dated May 13, 2015.
U.S. Appl. No. 13/836,495—Office Action, dated Jun. 16, 2015.
U.S Appl. No. 13/835,467—Office Action, dated Dec. 8, 2015.
U.S. Appl. No. 15/093,848—Office Action, dated Jun. 28, 2016.
U.S. Appl. No. 14/560,250—Office Action, dated Aug. 25, 2016.
U.S. Appl. No. 15/093,848—Office Action, dated Oct. 7, 2016.
U.S. Appl. No. 14/837,575—Office Action, dated Feb. 2, 2017.
U.S. Appl. No. 14/560,250—Office Action, dated Feb. 13, 2017.
U.S. Appl. No. 14/837,575—Office Action, dated May 4, 2017.

ADMIXTURE AND METHOD FOR FREEZE-THAW DAMAGE RESISTANCE AND SCALING DAMAGE RESISTANCE OF CEMENTITIOUS COMPOSITIONS

This application is a continuation application of U.S. Ser. No. 13/835,467 filed on Mar. 15, 2013, which claims the benefit of the filing date under 35 U.S.C. § 119(e) of U.S. Provisional Applications For patent Ser. No. 61/635,562 filed on Apr. 19, 2012 and Ser. No. 61/695,134 filed on Aug. 30, 2012, which applications are incorporated by reference herein.

Provided are a freeze-thaw damage resistance and scaling damage resistance admixture and a method of preparing a freeze-thaw damage resistant and scaling damage resistant cementitious composition.

Freeze-thaw cycles can be extremely damaging to water-saturated hardened cementitious compositions, such as concrete. The best known technique to prevent or reduce the damage done is the incorporation in the composition of microscopically fine pores or voids. The pores or voids function as internal expansion chambers and can therefore protect the composition from freeze-thaw damage by relieving changes in hydraulic pressure caused by freeze-thaw cycling. A conventional method used for producing such voids in cementitious compositions is by introducing air-entraining agents into the compositions, which stabilize tiny bubbles of air that are entrapped in the composition during mixing.

Unfortunately, this approach of producing air voids in cementitious compositions is plagued by a number of production and placement issues, some of which are the following:

Air Content: Changes in air content of the cementitious composition can result in a composition with poor resistance to freeze-thaw damage if the air content drops with time or reduce the compressive strength of the composition if the air content increases with time. Examples are pumping a cementitious composition (decreasing air content by compression), job-site addition of a superplasticizer (often elevates air content or destabilizes the air void system), and interaction of specific admixtures with the air-entraining surfactant (that could increase or decrease air content).

Air Void Stabilization: The inability to stabilize air bubbles may be caused by the presence of materials that adsorb the stabilizing surfactant, i.e., fly ash having high surface area carbon or insufficient water for the surfactant to work properly, i.e, low slump concrete.

Air Void Characteristics: Formation of bubbles that are too large to provide resistance to freezing and thawing damage may be the result of poor quality or poorly graded aggregates, use of other admixtures that destabilize the bubbles, etc. Such voids are often unstable and tend to float to the surface of the fresh concrete.

Overfinishing: Removal of air by overfinishing, removes air from the surface of the concrete, typically resulting in distress by scaling of the detrained zone of cement paste adjacent to the overfinished surface.

The generation and stabilization of air at the time of mixing and ensuring it remains at the appropriate amount and air void size until the cementitious composition hardens remain the largest day-to-day challenges for the cementitious composition producer in North America. The air content and the characteristics of the air void system entrained into the cementitious composition cannot be controlled by direct quantitative means, but only indirectly through the amount and/or type of air-entraining agent added to the composition. Factors such as the composition and particle shape of the aggregates, the type and quantity of cement in the mix, the consistency of the cementitious composition, the type of mixer used, the mixing time, and the temperature all influence the performance of the air-entraining agent. The void size distribution in ordinary air-entrained concrete can show a very wide range of variation, between 10 and 3,000 micrometers (µm) or more. In such cementitious compositions, besides the small voids which are essential to cyclic freeze-thaw damage resistance, the presence of larger voids, which contribute little to the durability of the cementitious composition and could reduce the strength of the composition, has to be accepted as an unavoidable feature.

Air-entraining agents have been shown to provide resistance to freeze-thaw damage, as well as scaling damage resistance, which occurs when the surface of the hardened cementitious composition breaks away for any of a number of reasons, some of which are discussed above. However, because conventional air-entraining agents suffer from the problems discussed above, the cementitious composition industry is searching for new and better admixtures to provide the properties which are currently provided by conventional air-entraining agents.

A recent development is to use polymeric microspheres to create controlled-size voids within cementitious compositions. However, development is still ongoing to improve the function of polymeric microspheres within cementitious compositions, and to reduce the cost of including polymeric microspheres in cementitious compositions.

It has been found that, while polymeric microspheres are capable of providing resistance to freeze-thaw damage similarly to or better than conventional air-entraining agents, polymeric microspheres may not be able to provide the degree of scaling damage resistance provided by conventional air-entraining agents. Freeze-thaw damage resistance of cementitious compositions is tested via ASTM C-666, and scaling damage resistance during freeze-thaw cycling is tested via ASTM C-672, both of which are incorporated herein by reference.

Furthermore, in order to provide appropriately sized air voids, polymeric microspheres may need to be expanded prior to incorporation into cementitious compositions. After expansion, expanded polymeric microspheres may have up to about 75 times the volume of the unexpanded microspheres. Providing cementitious composition admixtures which include expanded polymeric microspheres can be expensive, due to the high shipping cost associated with shipping an admixture which includes high-volume expanded microspheres, particularly if provided in an aqueous slurry which may include a volume of water.

What is needed is a cementitious composition admixture comprising polymeric microspheres, and optionally additional components, which provides adequate resistance to freeze-thaw damage and/or scaling damage, and a method to provide the polymeric microspheres into the cementitious composition at a reasonable price.

Embodiments of the subject matter are disclosed with reference to the accompanying drawings and are for illustrative purposes only. The subject matter is not limited in its application to the details of construction or the arrangement of the components illustrated in the drawings. Like reference numerals are used to indicate like components, unless otherwise indicated.

Figure 1:
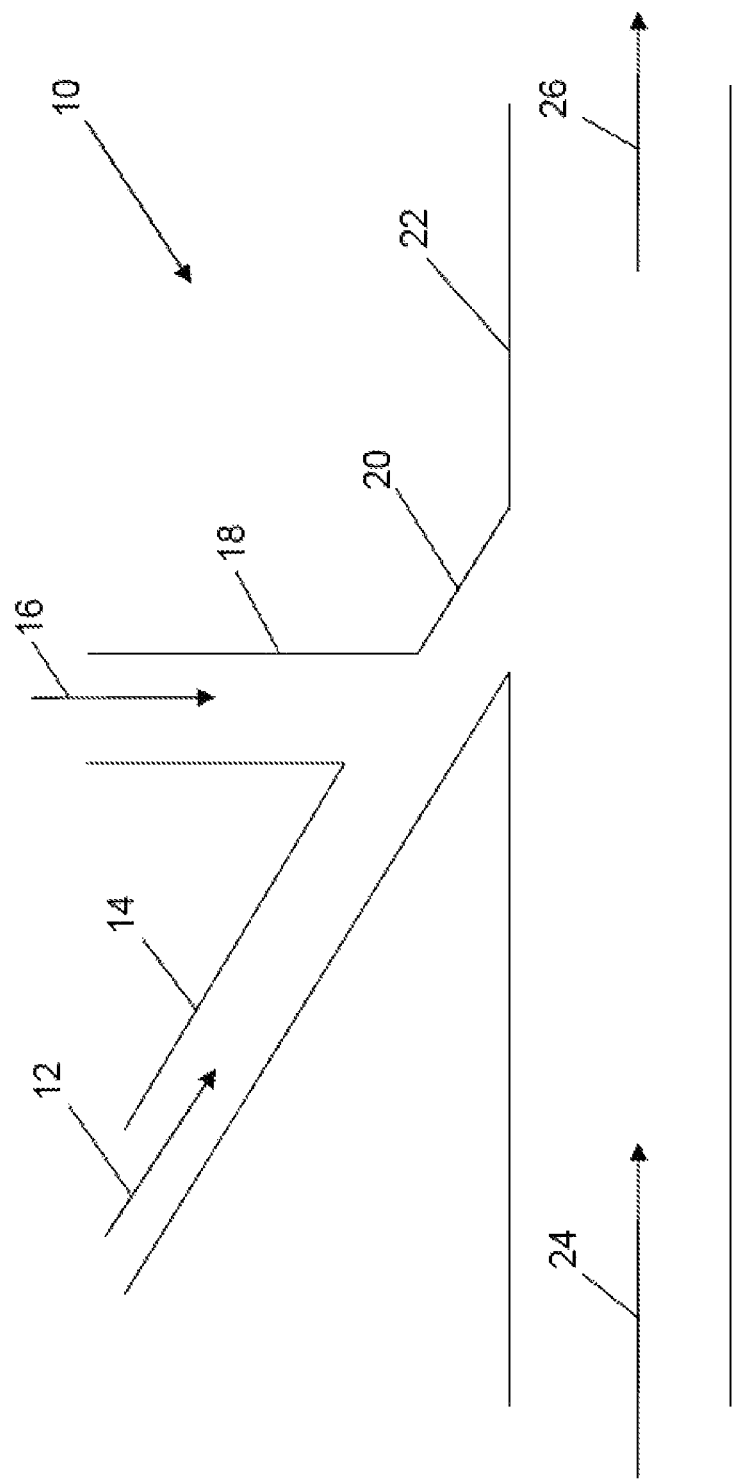
FIG. 1 is a schematic diagram of an embodiment of an apparatus for performing the subject method(s).

A freeze-thaw damage resistance and/or scaling damage resistance admixture for a cementitious composition is provided, comprising an aqueous slurry comprising a water insoluble superabsorbent polymer and expandable polymeric microspheres. A method for preparing a freeze-thaw damage resistant and/or scaling damage resistant cementitious composition is also provided, comprising forming a mixture of a hydraulic cement and an admixture comprising an aqueous slurry of a water insoluble superabsorbent polymer and expanded polymeric microspheres.

The expanded polymeric microspheres provide void spaces in cementitious compositions prior to final setting, and such void spaces act to increase the freeze-thaw durability of the cementitious material. Expanded polymeric microspheres introduce voids into cementitious compositions to produce a fully formed void structure in cementitious compositions which resists concrete degradation produced by water-saturated cyclic freezing and does not rely on air bubble stabilization during mixing of cementitious compositions. The freeze-thaw durability enhancement produced with the expanded polymeric microspheres is based on a physical mechanism for relieving stresses produced when water freezes in a cementitious material. In conventional practice, properly sized and spaced voids are generated in the hardened material by using chemical admixtures to stabilize the air voids entrained into a cementitious composition during mixing. In conventional cementitious compositions these chemical admixtures as a class are called air entraining agents. The present admixture utilizes expanded polymeric microspheres to form a void structure in cementitious compositions and does not require the production and/or stabilization of air entrained during the mixing process.

The use of expanded polymeric microspheres substantially eliminates some of the practical problems encountered in the current art. It also makes it possible to use some materials, i.e., low grade, high-carbon fly ash, which may be landfilled as they are considered unusable in air-entrained cementitious compositions without further treatment. This results in cement savings, and therefore economic savings. As the voids "created" by this approach are much smaller than those obtained by conventional air-entraining agents, the volume of expanded polymeric microspheres that is required to achieve the desired durability is also much lower than in conventional air entrained cementitious compositions. Therefore, a higher compressive strength can be achieved with the present admixtures and methods at the same level of protection against freezing and thawing damage. Consequently, the most expensive component used to achieve strength, i.e., cement, can be saved.

The expandable polymeric microspheres may be comprised of a polymer that is at least one of polyethylene, polypropylene, polymethyl methacrylate, poly-o-chlorostyrene, polyvinyl chloride, polyvinylidene chloride, polyacrylonitrile, polymethacrylonitrile, polystyrene, and copolymers thereof, such as copolymers of vinylidene chloride-acrylonitrile, polyacrylonitrile-copolymethacrylonitrile, polyvinylidene chloride-polyacrylonitrile, or vinyl chloride-vinylidene chloride, and the like. As the microspheres are composed of polymers, the wall may be flexible, such that it moves in response to pressure. The material from which the microspheres are to be made, therefore, may be flexible, and, in certain embodiments, resistant to the alkaline environment of cementitious compositions. Without limitation, suitable expandable polymeric microspheres are available from Eka Chemicals Inc., an Akzo Nobel company (Duluth, Ga.), under the trade name EXPANCEL®.

In certain embodiments, the unexpanded, expandable polymeric microspheres may have an average diameter of about 100 µm or less, in certain embodiments about 50 µm or less, in certain embodiments about 24 µm or less, in certain embodiments about 16 µm or less, in certain embodiments about 15 µm or less, in certain embodiments about 10 µm or less, and in other embodiments about 9 µm or less. In certain embodiments, the average diameter of the unexpanded polymeric microspheres may be from about 10 µm to about 16 µm, in certain embodiments from about 6 µm to about 9 µm, in certain embodiments from about 3 µm to about 6 µm, in certain embodiments from about 9 µm to about 15 µm, and in other embodiments from about 10 µm to about 24 µm. The polymeric microspheres may have a hollow core and compressible wall. The interior portion of the polymeric microspheres comprises a void cavity or cavities that may contain gas (gas filled) or liquid (liquid filled).

In certain embodiments, the expanded, expandable polymeric microspheres may have an average diameter of about 200 to about 900 µm, in certain embodiments, about 40 to about 216 µm, in certain embodiments about 36 to about 135 µm, in certain embodiments about 24 to about 81 µm, and in certain embodiments about 12 to about 54 µm.

It has been found that the smaller the diameter of the expandable polymeric microspheres, the smaller the amount of the microspheres that is required to achieve the desired freeze-thaw damage resistance in cementitious compositions. This is beneficial from a performance perspective, in that a smaller decrease in compressive strength occurs by the addition of the microspheres, as well as an economic perspective, since a smaller amount of spheres is required. Similarly, the wall thickness of the polymeric microspheres may be optimized to minimize material cost, but to ensure that the wall thickness is adequate to resist damage and/or fracture during mixing, placing, consolidating and finishing processes of the cementitious composition.

Scaling damage resistance is a result of the density of the cementitious composition at the surface of the composition. Greater density of the surface of a hardened cementitious composition results in increased scaling damage resistance. In some cementitious applications, water soluble viscosity modifying admixtures ("VMAs") are considered scaling-damage-resistance-neutral, or even as improving scaling damage resistance.

It has been surprisingly found that water soluble VMAs may lead to increased scaling damage in cementitious compositions without entrained air. Without wishing to be limited by theory, it is thought that the water soluble VMA molecules have high affinity with water molecules, which permits the water to act as "free" water. The "free" water can migrate to the surface of the cementitious composition during placement and hardening (known as "bleeding"), reducing the density of the surface of the cementitious composition, which may result in scaling damage. Thus, as bleeding increases, scaling damage may increase.

Water insoluble superabsorbent polymers ("SAPs"), however, have been found to decrease bleeding. Without wishing to be limited by theory, it is thought that water insoluble SAPs capture "free" water in the cementitious composition, and thereby reduce bleeding. This results in increased scaling damage resistance.

The following examples illustrate how water soluble VMAs and water insoluble SAPs affect bleeding in cementitious compositions, and should not be construed to limit the present subject matter in any manner.

Examples 1-5 were designed to test the affect of a water soluble cellulose ether viscosity modifying agent on bleeding in a cementitious composition. Example 1 had no water soluble cellulose ether, and Examples 2-5 had the amounts of water soluble cellulose ether shown in Table 1.

TABLE 1

| | Example No. | | | | |
|---|---|---|---|---|---|
| | 1 | 2 | 3 | 4 | 5 |
| Water soluble cellulose ether (% cwt*) | 0.0000 | 0.0013 | 0.0026 | 0.0039 | 0.0117 |
| % Bleed | 3.67 | 4.05 | 4.08 | 3.88 | 3.97 |

*% cwt is the percentage of water soluble cellulose ether based on the total amount of cement present in the cementitious composition.

Table 1 shows that water soluble cellulose ether may increase the percentage of bleed in certain cementitious compositions.

Examples 6-10 were designed to test the affect of a water soluble biopolymer viscosity modifying agent on bleeding in a cementitious composition. Example 6 had no water soluble biopolymer, and Examples 7-10 had the amounts of water soluble biopolymer shown in Table 2.

TABLE 2

| | Example No. | | | | |
|---|---|---|---|---|---|
| | 6 | 7 | 8 | 9 | 10 |
| Water soluble biopolymer (% cwt*) | 0.0000 | 0.0013 | 0.0026 | 0.0039 | 0.0117 |
| % Bleed | 4.41 | 4.55 | 4.74 | 4.64 | 4.70 |

*% cwt is the percentage of water soluble biopolymer based on the total amount of cement present in the cementitious composition.

Table 2 shows that water soluble biopolymer may increase the percentage of bleed in certain cementitious compositions.

Examples 11-18 were designed to test the affect of a water soluble polymer viscosity modifying agent on bleeding in a cementitious composition. Examples 11 and 12 had no water soluble biopolymer, but had 5.1% and 1.1% entrained air, respectively. Examples 13-18 had the amounts of water soluble polymer shown in Table 3.

TABLE 3

| | Example No. | | | | | | | |
|---|---|---|---|---|---|---|---|---|
| | 11 | 12 | 13 | 14 | 15 | 16 | 17 | 18 |
| Water soluble polymer (% cwt*) | 0.0000 | 0.0000 | 0.0130 | 0.0261 | 0.0522 | 0.0782 | 0.1043 | 0.1304 |
| % Bleed | 4.38 | 5.82 | 5.64 | 5.81 | 6.89 | 7.15 | 7.52 | 8.32 |

*% cwt is the percentage of water soluble polymer based on the total amount of cement present in the cementitious composition.

Table 3 shows that water soluble polymer may increase the percentage of bleed in certain cementitious compositions.

Examples 19-26 were designed to test the affect of a water insoluble superabsorbent polymer on bleeding in a cementitious composition. Examples 19 and 20 had no water soluble biopolymer, but had 6.6% and 1.8% entrained air, respectively. Examples 21-26 had the amounts of water insoluble superabsorbent polymer shown in Table 4.

TABLE 4

| | Example No. | | | | | | | |
|---|---|---|---|---|---|---|---|---|
| | 19 | 20 | 21 | 22 | 23 | 24 | 25 | 26 |
| Water insoluble SAP (% cwt*) | 0.0000 | 0.0000 | 0.0575 | 0.0575 | 0.1150 | 0.1150 | 0.2301 | 0.2301 |
| % Bleed | 2.46 | 3.74 | 3.17 | 3.31 | 2.83 | 2.92 | 2.10 | 1.93 |

*% cwt is the percentage of water insoluble superabsorbent polymer based on the total amount of cement present in the cementitious composition.

Table 4 shows that water insoluble superabsorbent polymer may generally decrease the percentage of bleed in certain cementitious compositions.

We have found that water insoluble superabsorbent polymers also stabilize aqueous slurries comprising expandable polymeric particles. Therefore, the water insoluble superabsorbent polymers may be used for scaling damage resistance and/or admixture stabilization according to the present subject matter.

SAPs include cross-linked polyelectrolytes which swell upon contact with water or aqueous solutions, resulting in the formation of a hydrogel. In one process, SAPs may be produced via an endless belt reactor or a kneader. The process begins with an aqueous monomer solution which is polymerized via the endless belt reactor or the kneader. In the case of the endless belt reactor, the solution is poured out at the start of the belt, and polymerization is completed adiabatically, forming a hard rubber-like gel. At the end of the belt, an extruder cuts the gel into small pieces, which are then dried and ground to the desired particle size. In the case of the kneader, the polymerization and cutting of the gel are completed in a single step.

In another process, SAPs are produced via inverse suspension polymerization. In this process, the aqueous monomer solution is suspended in an inorganic solvent, such as hexane or cyclohexane. The suspension is polymerized, and water may be removed via azeotropic distillation. The product is filtered off and dried, leaving the SAP product.

SAP molecules and/or particles comprise ions which are forced closely together by the polymer network, resulting in increased osmotic pressure. When the SAP molecule/particle comes into contact with water, the ions are diluted in the water, thereby relieving the osmotic pressure.

Suitable superabsorbent polymers include cross-linked polyelectrolytes, such as cross-linked polyacrylic, cross-linked polyacrylamide, or covalently cross-linked acrylamide/acrylic acid copolymers. In certain embodiments, the admixtures and/or methods described herein may include one or more than one of the foregoing superabsorbent polymers.

In certain embodiments, the size of the superabsorbent polymer particles which may be included in the admixtures and/or methods described herein is from about 5 μm to about 1,000 μm, in further embodiments from about 5 μm to about 500 μm, and in still further embodiments, from about 5 μm to about 300 μm.

In certain embodiments, the amount of unexpanded, expandable polymeric microspheres to be included in the admixture may be from about 10 to about 99.9 percent by weight, based on the total weight of ingredients of the admixture other than water. In other embodiments, the amount of expandable polymeric microspheres to be included in the admixture may be from about 50 to about 99.9 percent by weight, based on the total weight of ingredients of the admixture other than water. In further embodiments, the amount of expandable polymeric microspheres to be included in the admixture may be from about 80 to about 99.9 percent by weight, based on the total weight of ingredients of the admixture other than water.

In certain embodiments, the amount of water insoluble superabsorbent polymer to be included in the admixture may be from about 0.1 to about 30 percent by weight, based on the total weight of ingredients of the admixture other than water. In other embodiments, the amount of water insoluble superabsorbent polymer to be included in the admixture may be from about 0.1 to about 20 percent by weight, based on the total weight of ingredients of the admixture other than water. In further embodiments, the amount of water insoluble superabsorbent polymer to be included in the admixture may be from about 0.1 to about 10 percent by weight, based on the total weight of ingredients of the admixture other than water.

In certain embodiments, the amount of unexpanded, expandable polymeric microspheres to be included in the admixture may be from about 10 to about 99.9 percent by volume, based on the total volume of ingredients of the admixture other than water. In other embodiments, the amount of expandable polymeric microspheres to be included in the admixture may be from about 50 to about 99.9 percent by volume, based on the total volume of ingredients of the admixture other than water. In further embodiments, the amount of expandable polymeric microspheres to be included in the admixture may be from about 80 to about 99.9 percent by volume, based on the total volume of ingredients of the admixture other than water.

In certain embodiments, the amount of water insoluble superabsorbent polymer to be included in the admixture may be from about 0.1 to about 30 percent by volume, based on the total volume of ingredients of the admixture other than water. In other embodiments, the amount of water insoluble superabsorbent polymer to be included in the admixture may be from about 0.1 to about 20 percent by volume, based on the total volume of ingredients of the admixture other than water. In further embodiments, the amount of water insoluble superabsorbent polymer to be included in the admixture may be from about 0.1 to about 10 percent by volume, based on the total volume of ingredients of the admixture other than water.

The ratio of the amount of unexpanded, expandable polymeric particles to the amount of water insoluble superabsorbent polymer present in the admixture may be from about 100:1 to about 6:1 by weight, in certain embodiments from about 50:1 to about 10:1 by weight, in further embodiments from about 30:1 to about 20:1 by weight.

The ratio of the amount of unexpanded, expandable polymeric particles to the amount of water insoluble superabsorbent polymer present in the admixture may be from about 100:1 to about 3:1 by volume, in certain embodiments from about 50:1 to about 6:1 by volume, in further embodiments from about 30:1 to about 10:1 by volume.

The hydraulic cement may be a Portland cement, a calcium aluminate cement, a magnesium phosphate cement, a magnesium potassium phosphate cement, a calcium sulfoaluminate cement or any other suitable hydraulic binder. Aggregate may be included in the cementitious composition. The aggregate can be silica, quartz, sand, crushed marble, glass spheres, granite, limestone, calcite, feldspar, alluvial sands, any other durable aggregate, and mixtures thereof.

In certain embodiments, the amount of expanded, expandable polymeric microspheres to be included in the cementitious composition, delivered via the admixtures and/or methods described herein, may be from about 0.002 to about 0.06 percent by weight, based on the total weight of the cementitious composition. In other embodiments, the amount of expandable polymeric microspheres to be included in the cementitious composition, delivered via the admixture, may be from about 0.005 to about 0.04 percent by weight, based on the total weight of the cementitious composition. In further embodiments, the amount of expandable polymeric microspheres to be included in the cementitious composition, delivered via the admixture, may be from about 0.008 to about 0.03 percent by weight, based on the total weight of the cementitious composition.

In certain embodiments, the amount of water insoluble superabsorbent polymer to be included in the cementitious composition, delivered via the admixtures and/or methods described herein, may be from about 0.00002 to about 0.02 percent by weight, based on the total weight of the cementitious composition. In other embodiments, the amount of water insoluble superabsorbent polymer to be included in the cementitious composition, delivered via the admixture, may be from about 0.00005 to about 0.013 percent by weight, based on the total weight of the cementitious composition. In further embodiments, the amount of water insoluble superabsorbent polymer to be included in the cementitious composition, delivered via the admixture, may be from about 0.00008 to about 0.01 percent by weight, based on the total weight of the cementitious composition.

In certain embodiments, the amount of expanded, expandable polymeric microspheres to be included in the cementitious composition, delivered via the admixtures and/or methods described herein, may be from about 0.2 to about 4 percent by volume, based on the total volume of the cementitious composition. In certain embodiments, the amount of expanded, expandable polymeric microspheres to be included in the cementitious composition, delivered via the subject admixtures or methods, may be from about 0.25 to about 4 percent by volume, based on the total volume of the cementitious composition. In certain embodiments, the amount of expanded, expandable polymeric microspheres to be included in the cementitious composition, delivered via the subject admixtures or methods, may be from about 0.4 to about 4 percent by volume, based on the total volume of the cementitious composition. In certain embodiments, the amount of expanded, expandable polymeric microspheres to be included in the cementitious composition, delivered via the subject admixtures or methods, may be from about 0.25 to about 3 percent by volume, based on the total volume of the cementitious composition. In certain embodiments, the amount of expanded, expandable polymeric microspheres to be included in the cementitious composition, delivered via the subject admixtures or methods, may be from about 0.5 to about 3 percent by volume, based on the total volume of the cementitious composition.

In certain embodiments, the amount of water insoluble superabsorbent polymer to be included in the cementitious composition, delivered via the admixtures and/or methods described herein, may be from about 0.002 to about 0.1 percent by volume, based on the total volume of the cementitious composition. In other embodiments, the amount of water insoluble superabsorbent polymer to be included in the cementitious composition, delivered via the admixture, may be from about 0.005 to about 0.1 percent, or about 0.02 to about 0.1 by volume, based on the total volume of the cementitious composition. In further embodiments, the amount of water insoluble superabsorbent polymer to be included in the cementitious composition, delivered via the admixture, may be from about 0.008 to about 0.08 percent by volume, based on the total volume of the cementitious composition.

A method of expanding expandable polymeric microspheres is also provided, comprising contacting an aqueous slurry comprising unexpanded, expandable polymeric microspheres with steam proximate to and/or during manufacture of a cementitious composition, wherein the aqueous slurry optionally further comprises an admixture for the cementitious composition. In certain embodiments, the method may comprise contacting an aqueous slurry comprising unexpanded, expandable polymeric microspheres with steam in-situ during manufacture of a cementitious composition.

The process of "contacting an aqueous slurry comprising unexpanded, expandable polymeric microspheres with steam proximate to and/or during manufacture of a cementitious composition", may include at least one of: (i) contacting the aqueous slurry comprising the unexpanded, expandable polymeric microspheres with steam immediately prior to introducing, such as by injecting, the aqueous slurry into a feed water stream being fed into a cementitious composition during manufacture of the cementitious composition; or (ii) contacting the aqueous slurry comprising the unexpanded, expandable polymeric microspheres with steam to expand the expandable polymeric microspheres and quenching the expanded expandable polymeric microspheres into water at a cementitious composition manufacturing facility, and reserving the quenched, expanded microsphere-containing aqueous slurry for introduction into a cementitious composition manufactured at the facility. As used herein, "at a cementitious composition manufacturing facility" means that expansion of the unexpanded, expandable polymeric microspheres occurs at the same facility or at an adjacent or proximate facility where the cementitious composition is manufactured.

Referring to FIG. 1, in certain embodiments, the aqueous slurry 12 comprising unexpanded, expandable polymeric microspheres is fed through a first conduit 14, while at the same time steam 16 is fed through a second conduit 18. The first 14 and second 18 conduits meet 20 immediately prior to feeding into a third conduit 22, which contains feed water 24 flowing 26 into a cementitious composition mixture. The meeting of the first and second conduits results in rapid heating of the unexpanded, expandable polymeric microspheres, causing the microspheres to expand. The expanded microspheres are then quenched by the feed water flowing through the third conduit 22, which allows the expanded microspheres to retain their size upon introduction into the cementitious composition mixture. In certain embodiments, the third conduit 22 may be flowing 26 into a reservoir vessel (not shown) and reserved for later introduction into a cementitious composition. In an alternative embodiment, the third conduit 22 may be eliminated, and the expanded microspheres may be introduced directly into an on-site reservoir vessel (not shown) and reserved for later introduction into a cementitious composition after being contacted by the steam in the second conduit 18. In certain embodiments, the expanded microspheres may have a volume which is up to about 75 times larger than their original, unexpanded volume.

Figure 2:
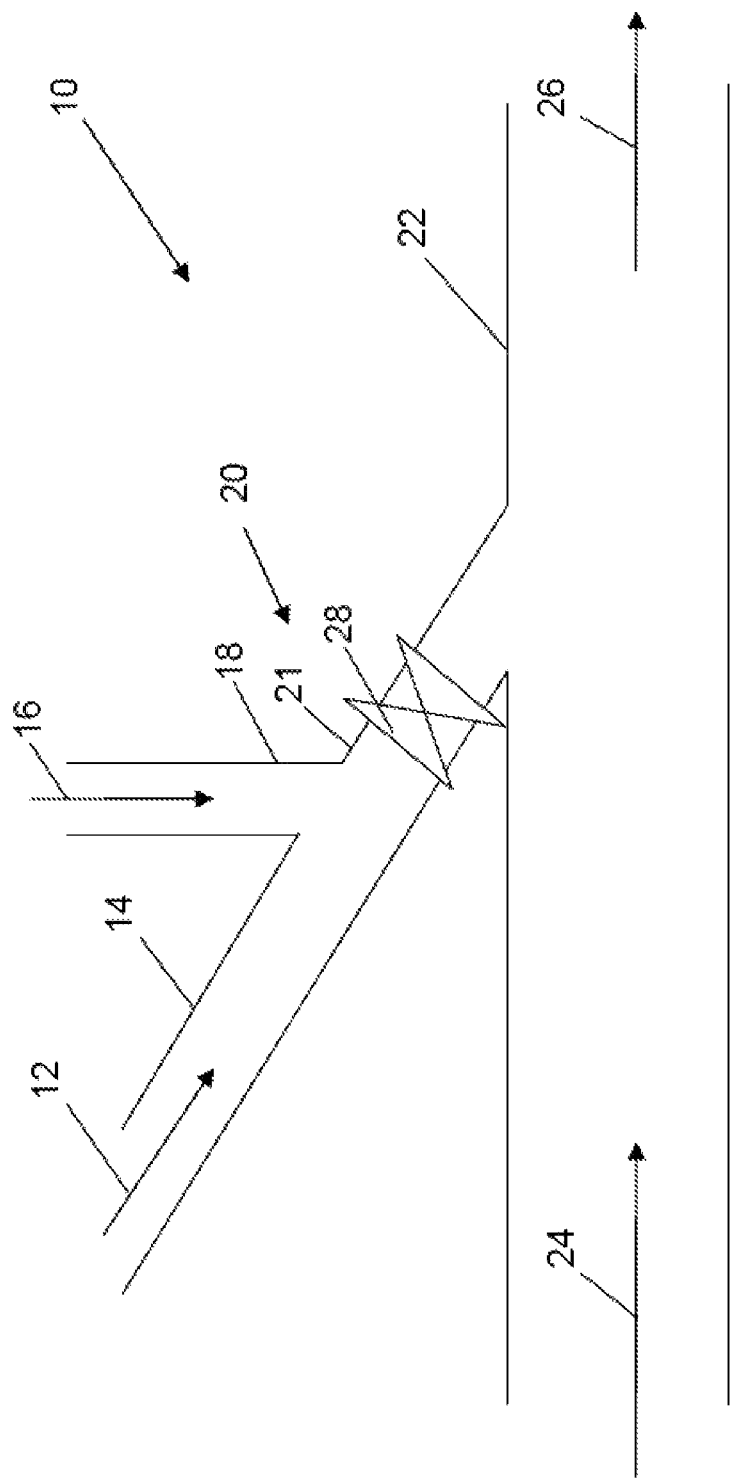
FIG. 2 is a schematic diagram of an embodiment of an apparatus for performing the subject method(s).

Referring to FIG. 2, in certain embodiments, the meeting 20 of the first 14 and second 18 conduits may comprise a fourth conduit 21. The fourth conduit 21 may include a back pressure generator 28, such as a flow control valve or a flow restriction device, such as an orifice nozzle. The back pressure generator 28 is capable of restricting and/or controlling the flow of the mixture of the aqueous slurry 12 and the steam 16 in order to ensure that the mixture achieves the proper pressure and temperature required to adequately expand the expandable microspheres in the aqueous slurry 12. In certain embodiments, the back pressure generator 28 may also at least partially prevent backflow of the feed water 24 from the third conduit 22.

In certain embodiments, the present admixture may be prepared using an apparatus comprising: (a) a steam generator or other source of steam; (b) a steam conduit in fluid communication with the steam generator or other steam source; (c) a fluid material conduit in fluid communication with a source of a fluid material, wherein the fluid material comprises unexpanded, expandable polymeric microspheres and optionally water insoluble superabsorbent polymer; (d) a treatment zone in fluid communication with the steam generator or other steam source via the steam conduit, and with the fluid material conduit, such that the fluid material is contacted by steam within the treatment zone; and (e) a back pressure generator in fluid communication with the treatment zone, capable of increasing pressure in the treatment zone, which results in expansion of the expandable polymeric microspheres when the fluid material exits the treatment zone.

The fluid material comprising the unexpanded, expandable polymeric microspheres may also include components such as dispersants, surfactants, anti-caking agents, and/or film forming agents, as well as optionally the water insoluble superabsorbent polymer.

In one embodiment, a fluid material including water, the unexpanded, expandable polymeric microspheres, and optionally the water insoluble superabsorbent polymer to be included in the admixture for cementitious compositions is contacted with steam within the treatment zone, such that the unexpanded, expandable polymeric microspheres are subjected to increased temperature and pressure, which results in pre-expansion of the expandable polymeric microspheres. Upon exiting the treatment zone, optionally via the back pressure generator, the expandable polymeric microspheres experience a pressure drop equal to the difference between the pressure in the treatment zone and the pressure in the environment outside the treatment zone. This sudden decrease in pressure results in rapid expansion of the expandable polymeric microspheres.

The back pressure generator is capable of restricting and/or controlling the flow of the fluid material and steam through the treatment zone, to ensure that the temperature and pressure within the treatment zone are sufficient to provide enough of a pressure drop to allow the expandable polymeric microspheres to expand to a desired degree upon exiting the back pressure generator. The back pressure generator may comprise, for example, a flow control valve or a flow restriction device, such as an orifice nozzle.

In certain embodiments, the temperature inside the treatment zone may be from about 105° C. (221° F.) to about 145° C. (293° F.), in certain embodiments from about 135° C. (275° F.) to about 145° C. (293° F.). In certain embodiments, the pressure inside the treatment zone may be from about 120 kPa (17.4 psi) to about 420 kPa (60.9 psi), in certain embodiments from about 315 kPa (45.7 psi) to about 420 kPa (60.9 psi).

The fluid material comprising the expanded, expandable polymeric microspheres may be added to or mixed with process water or other liquid admixtures, and then incorporated into the cementitious composition. Thus, the treated fluid material may contain both the expanded, expandable polymeric microspheres and the water insoluble superabsorbent polymer, or may contain the expanded, expandable polymeric microspheres and be mixed with a liquid admixture, such as a dispersion containing the water insoluble superabsorbent polymer. Alternatively, the fluid material comprising the expanded, expandable polymeric microspheres and the water insoluble superabsorbent polymer may be incorporated directly into a cementitious composition (before or during mixing of the cementitious composition) without first adding the treated fluid material to process water or other liquid admixtures.

The present methods may be performed on-site at cementitious composition manufacturing facilities, such as ready-mix concrete plants. Such facilities may include storage areas for cement, water, and other components to be added to the cementitious compositions being produced, such as aggregate and/or cementitious composition admixtures. At the facilities, the various components of cementitious compositions, such as cement, water, aggregate, and/or admixtures are mixed together to form a cementitious composition. The mixing may be performed on a mixing truck, such as a concrete mixing truck. Once the components are mixed, the cementitious composition may be transported to a job site, where the composition is placed and allowed to harden. The cementitious composition may also be utilized to manufacture cementitious articles, such as concrete block or concrete pavers, on-site at the cementitious composition manufacturing facilities or at another facility.

In certain embodiments, the present admixtures and methods allow for an aqueous slurry of expandable polymeric microspheres and/or an admixture comprising unexpanded, expandable polymeric microspheres to be shipped to cementitious composition manufacturing facilities at minimal cost. Once the aqueous slurry and/or admixture containing the unexpanded, expandable polymeric microspheres arrives at such a facility, the expandable polymeric microspheres may be expanded on-site. As compared with shipping slurries and/or admixtures which contain expanded expandable polymeric microspheres, which may have a volume of up to 75 times greater than unexpanded microspheres, shipping slurries and/or admixtures which contain unexpanded expandable microspheres drastically reduces shipping costs, which could equal or exceed the actual cost of the admixture. Furthermore, other logistical costs, such as storage, may also be reduced.

In certain embodiments, a cementitious composition comprising 1.5% by volume, based on the total volume of the cementitious composition, of expanded expandable polymeric microspheres may have a 30% higher 28-day compressive strength as compared to a cementitious composition comprising a conventional air-entraining agent, yet can also pass ASTM C 666, which is incorporate herein by reference.

An admixture composition described herein may contain other admixtures or ingredients and should not be necessarily limited to the stated formulations. A cementitious composition provided by the method(s) described herein may contain other admixtures or ingredients and should not be necessarily limited to the stated formulations. These admixtures and/or ingredients that may be added include, but are not limited to: dispersants, set and strength accelerators/enhancers, set retarders, water reducers, corrosion inhibitors, wetting agents, water soluble polymers, rheology modifying agents, water repellents, non degrading fibers, dampproofing admixtures, permeability reducers, fungicidal admixtures, germicidal admixtures, insecticide admixtures, alkali-reactivity reducer, bonding admixtures, shrinkage reducing admixtures, and any other admixture or additive suitable for use in cementitious compositions. The admixtures and cementitious compositions described herein need not contain any of the foregoing components, but may contain any number of the foregoing components.

Aggregate can be included in the cementitious composition to provide mortars which include fine aggregate, and concretes which include fine and coarse aggregates. The fine aggregates are materials that almost entirely pass through a Number 4 sieve (ASTM C 125 and ASTM C 33), such as silica sand. The coarse aggregates are materials that are predominantly retained on a Number 4 sieve (ASTM C 125 and ASTM C 33), such as silica, quartz, crushed marble, glass spheres, granite, limestone, calcite, feldspar, alluvial sands, sands or any other durable aggregate, and mixtures thereof.

A pozzolan is a siliceous or aluminosiliceous material that possesses little or no cementitious value but will, in the presence of water and in finely divided form, chemically react with the calcium hydroxide produced during the hydration of Portland cement to form materials with cementitious properties. Diatomaceous earth, opaline cherts, clays, shales, fly ash, slag, silica fume, volcanic tuffs and pumicites are some of the known pozzolans. Certain ground granulated blast-furnace slags and high calcium fly ashes possess both pozzolanic and cementitious properties. Natural pozzolan is a term of art used to define the pozzolans that occur in nature, such as volcanic tuffs, pumices, trasses, diatomaceous earths, opaline, cherts, and some shales. Nominally inert materials can also include finely divided raw quartz, dolomites, limestones, marble, granite, and others. Fly ash is defined in ASTM C618.

If used, silica fume can be uncompacted or can be partially compacted or added as a slurry. Silica fume additionally reacts with the hydration byproducts of the cement binder, which provides for increased strength of the finished articles and decreases the permeability of the finished articles. The silica fume, or other pozzolans such as fly ash or calcined clay such as metakaolin, can be added to the cementitious wet cast mixture in an amount from about 5% to about 70% based on the weight of cementitious material.

A dispersant if used can be any suitable dispersant such as lignosulfonates, beta naphthalene sulfonates, sulfonated melamine formaldehyde condensates, polyaspartates, polycarboxylates with and without polyether units, naphthalene sulfonate formaldehyde condensate resins, or oligomeric dispersants.

Polycarboxylate dispersants can be used, by which is meant a dispersant having a carbon backbone with pendant side chains, wherein at least a portion of the side chains are attached to the backbone through a carboxyl group, an ether group, or an amide or imide group. The term dispersant is also meant to include those chemicals that also function as a plasticizer, high range water reducer, fluidizer, antiflocculating agent, or superplasticizer for cementitious compositions.

The term oligomeric dispersant refers to oligomers that are a reaction product of: component A, optionally component B, and component C; wherein each component A is independently a nonpolymeric, functional moiety that adsorbs onto a cementitious particle; wherein component B is an optional moiety, where if present, each component B is independently a nonpolymeric moiety that is disposed between the component A moiety and the component C moiety; and wherein component C is at least one moiety that is a linear or branched water soluble, nonionic polymer substantially non-adsorbing to cement particles. Oligomeric dispersants are disclosed in U.S. Pat. Nos. 6,133,347, 6,492,461, and 6,451,881.

Set and strength accelerators/enhancers that can be used include, but are not limited to: a nitrate salt of an alkali metal, alkaline earth metal, or aluminum; a nitrite salt of an alkali metal, alkaline earth metal, or aluminum; a thiocyanate of an alkali metal, alkaline earth metal or aluminum; an alkanolamine; a thiosulphate of an alkali metal, alkaline earth metal, or aluminum; a hydroxide of an alkali metal, alkaline earth metal, or aluminum; a carboxylic acid salt of an alkali metal, alkaline earth metal, or aluminum (preferably calcium formate); a polyhydroxylalkylamine; and/or a halide salt of an alkali metal or alkaline earth metal (preferably bromide).

The salts of nitric acid have the general formula $M(NO_3)_a$ where M is an alkali metal, or an alkaline earth metal or aluminum, and where a is 1 for alkali metal salts, 2 for alkaline earth salts, and 3 for aluminum salts. Preferred are nitric acid salts of Na, K, Mg, Ca and Al.

Nitrite salts have the general formula $M(NO_2)_a$ where M is an alkali metal, or an alkaline earth metal or aluminum, and where a is 1 for alkali metal salts, 2 for alkaline earth salts, and 3 for aluminum salts. Preferred are nitric acid salts of Na, K, Mg, Ca and Al.

The salts of the thiocyanic acid have the general formula $M(SCN)_b$, where M is an alkali metal, or an alkaline earth metal or aluminum, and where b is 1 for alkali metal salts, 2 for alkaline earth salts and 3 for aluminum salts. These salts are variously known as sulfocyanates, sulfocyanides, rhodanates or rhodanide salts. Preferred are thiocyanic acid salts of Na, K, Mg, Ca and Al.

Alkanolamine is a generic term for a group of compounds in which trivalent nitrogen is attached directly to a carbon atom of an alkyl alcohol. A representative formula is $N[H]_c[(CH_2)_dCHRCH_2R]_e$, where R is independently H or OH, c is 3-e, d is 0 to about 4 and e is 1 to about 3. Examples include, but are not limited to, are monoethanoalamine, diethanolamine, triethanolamine and triisopropanolamine.

The thiosulfate salts have the general formula $M_f(S_2O_3)_g$ where M is alkali metal or an alkaline earth metal or aluminum, and f is 1 or 2 and g is 1, 2 or 3, depending on the valencies of the M metal elements. Preferred are thiosulfate acid salts of Na, K, Mg, Ca and Al.

The carboxylic acid salts have the general formula RCOOM wherein R is H or $C_1$ to about $C_{10}$ alkyl, and M is alkali metal or an alkaline earth metal or aluminum. Preferred are carboxylic acid salts of Na, K, Mg, Ca and Al. An example of carboxylic acid salt is calcium formate.

A polyhydroxylalkylamine may have the general formula:

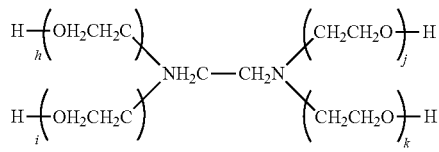

wherein h is 1 to 3, i is 1 to 3, j is 1 to 3, and k is 0 to 3. A preferred polyhydroxyalkylamine is tetrahydroxyethylethylenediamine.

Set retarding, or also known as delayed-setting or hydration control, admixtures are used to retard, delay, or slow the rate of setting of cementitious compositions. Set retarders are used to offset the accelerating effect of hot weather on the setting of cementitious compositions, or delay the initial set of cementitious compositions when difficult conditions of placement occur, or problems of delivery to the job site, or to allow time for special finishing processes. Most set retarders also act as low level water reducers and can also be used to entrain some air into cementitious compositions. Lignosulfonates, hydroxylated carboxylic acids, borax, gluconic, tartaric and other organic acids and their corresponding salts, phosphonates, certain carbohydrates such as sugars, polysaccharides and sugar-acids and mixtures thereof can be used as retarding admixtures.

Corrosion inhibitors serve to protect embedded reinforcing steel from corrosion. The high alkaline nature of cementitious compositions causes a passive and non-corroding protective oxide film to form on the steel. However, carbonation or the presence of chloride ions from deicers or seawater, together with oxygen can destroy or penetrate the film and result in corrosion. Corrosion-inhibiting admixtures chemically slow this corrosion reaction. The materials most commonly used to inhibit corrosion are calcium nitrite, sodium nitrite, sodium benzoate, certain phosphates or fluorosilicates, fluoroaluminates, amines, organic based water repelling agents, and related chemicals.

In the construction field, many methods of protecting cementitious compositions from tensile stresses and subsequent cracking have been developed through the years. One modern method involves distributing fibers throughout a fresh cementitious mixture. Upon hardening, this cementitious composition is referred to as fiber-reinforced cement. Fibers can be made of zirconium materials, carbon, steel, fiberglass, or synthetic materials, e.g., polypropylene, nylon, polyethylene, polyester, rayon, high-strength aramid, or mixtures thereof.

Dampproofing admixtures reduce the permeability of concrete that has low cement contents, high water-cement ratios, or a deficiency of fines in the aggregate portion. These admixtures retard moisture penetration into wet concrete and include certain soaps, stearates, and petroleum products.

Permeability reducers are used to reduce the rate at which water under pressure is transmitted through cementitious compositions. Silica fume, fly ash, ground slag, metakaolin, natural pozzolans, water reducers, and latex can be employed to decrease the permeability of the cementitious compositions.

Bacteria and fungal growth on or in hardened cementitious compositions may be partially controlled through the use of fungicidal, germicidal, and insecticidal admixtures. The most effective materials for these purposes are polyhalogenated phenols, dialdrin emulsions, and copper compounds.

Coloring admixtures are usually composed of pigments, either organic such as phthalocyanine or inorganic pigments such as metal-containing pigments that comprise, but are not limited to metal oxides and others, and can include, but are not limited to, iron oxide containing pigments, chromium oxide, aluminum oxide, lead chromate, titanium oxide, zinc white, zinc oxide, zinc sulfide, lead white, iron manganese black, cobalt green, manganese blue, manganese violet, cadmium sulfoselenide, chromium orange, nickel titanium yellow, chromium titanium yellow, cadmium sulfide, zinc yellow, ultramarine blue and cobalt blue.

Alkali-reactivity reducers can reduce the alkali-aggregate reaction and limit the disruptive expansion forces that this reaction can produce in hardened cementitious compositions. Pozzolans (fly ash, silica fume), blast-furnace slag, salts of lithium and barium are especially effective.

The shrinkage reducing agent which can be used comprises but is not limited to $RO(AO)_{1-10}H$, wherein R is a $C_{1-5}$ alkyl or $C_{5-6}$ cycloalkyl radical and A is a $C_{2-3}$ alkylene radical, alkali metal sulfate, alkaline earth metal sulfates, alkaline earth oxides, preferably sodium sulfate and calcium oxide.

The above listings of additional admixtures and additives are illustrative and not exhaustive or limiting.

It will be understood that the embodiments described herein are merely exemplary, and that one skilled in the art may make variations and modifications without departing from the spirit and scope of the invention. All such variations and modifications are intended to be included within the scope of the invention as described hereinabove. Further, all embodiments disclosed are not necessarily in the alternative, as various embodiments of the invention may be combined to provide the desired result.

What is claimed is:

1. A freeze-thaw damage resistance and scaling damage resistance admixture for a cementitious composition comprising a stabilized aqueous slurry comprising water insoluble superabsorbent polymer particles in an amount from 0.1 to 30 percent by weight, based on the total weight of ingredients of the admixture other than water, and unexpanded, expandable polymeric microspheres in an amount from 50 to 99.9 percent by weight, based on the total weight of ingredients of the admixture other than water, and wherein the expanded polymeric microspheres have an average diameter of from about 24 µm to about 900 µm.

2. The admixture of claim 1, wherein the polymeric microspheres comprise a polymer that is at least one of polyethylene, polypropylene, polymethyl methacrylate, poly-o-chlorostyrene, polyvinyl chloride, polyvinylidene chloride, polyacrylonitrile, polymethacrylonitrile, polystyrene, or copolymers or mixtures thereof.

3. The admixture of claim 1, wherein the polymeric microspheres comprise at least one copolymers of vinylidene chloride-acrylonitrile, polyacrylonitrile-copolymethacrylonitrile, polyvinylidene chloride-polyacrylonitrile, or vinyl chloride-vinylidene chloride, or mixtures thereof.

4. The admixture of claim 1, wherein the water insoluble superabsorbent polymer comprises at least one cross-linked polyelectrolyte.

5. The admixture of claim 4, wherein the at least one cross-linked polyelectrolyte is at least one of cross-linked polyacrylic, cross-linked polyacrylamide, or covalently cross-linked acrylamide/acrylic acid copolymers.

6. The admixture of claim 1, wherein the water insoluble superabsorbent polymer comprises water insoluble superabsorbent polymer particles, and wherein the average size of the water insoluble superabsorbent polymer particles is from about 5 µm to about 1,000 µm.

7. The admixture of claim 1, wherein the average size of the water insoluble superabsorbent polymer particles is from about 5 µm to about 300 µm.

8. The admixture of claim 1, wherein the expanded polymeric microspheres have an average diameter of from about 36 µm to about 900 µm.

9. The admixture of claim 1, wherein the expanded polymeric microspheres have an average diameter of from about 24 µm to about 216 µm.

10. The admixture of claim 1, wherein the expanded polymeric microspheres have an average diameter of from about 36 µm to about 216 µm.

11. A freeze-thaw damage resistant and/or scaling damage resistant cementitious composition comprising hydraulic cement and an admixture, wherein the admixture comprises a stabilized aqueous slurry comprising water insoluble superabsorbent polymer particles in an amount from 0.1 to 30 percent by weight, based on the total weight of ingredients of the admixture other than water, and expanded polymeric microspheres in an amount from 50 to 99.9 percent by weight, based on the total weight of ingredients of the admixture other than water, wherein the expanded polymeric microspheres have an average diameter of from about 24 µm to about 900 µm.

12. The cementitious composition of claim 11, comprising from 0.2 to 4 percent by volume expanded polymeric microspheres, based on the total volume of the cementitious composition.

13. The cementitious composition of claim 11, comprising from 0.25 to 3 percent by volume expanded polymeric microspheres, based on the total volume of the cementitious composition.

14. The cementitious composition of claim 11, comprising from 0.002 to 0.1 percent by volume water insoluble superabsorbent polymer, based on the total volume of the cementitious composition.

15. The cementitious composition of claim 11, comprising from 0.008 to 0.08 percent by volume water insoluble superabsorbent polymer, based on the total volume of the cementitious composition.

16. The cementitious composition of claim 11, comprising from 0.002 to 0.06 percent by weight expanded polymeric microspheres, based on the total weight of the cementitious composition.

17. The cementitious composition of claim 11, comprising from 0.00002 to 0.02 percent by weight water insoluble superabsorbent polymer, based on the total weight of the cementitious composition.

* * * * *